United States Patent [19]

Desbois

[11] Patent Number: 4,656,311

[45] Date of Patent: Apr. 7, 1987

[54] PROCESS FOR PREPARING HYDROXYLATED AROMATIC COMPOUNDS

[75] Inventor: Michel Desbois, Rillieux La Pape, France

[73] Assignee: Rhone-Poulenc Specialites Chimiques, France

[21] Appl. No.: 887,565

[22] Filed: Jul. 21, 1986

[30] Foreign Application Priority Data

Jul. 26, 1985 [FR] France ................................ 85 11437

[51] Int. Cl.$^4$ ............................................. C07C 39/24
[52] U.S. Cl. ...................................... 568/775; 568/774
[58] Field of Search ........................ 568/774, 726, 775

[56] References Cited

U.S. PATENT DOCUMENTS 3,629,340 12/1971 Wall et al. ............................ 568/775
4,524,032 6/1985 Misaki et al. ........................ 568/775

*Primary Examiner*—Werren B. Lone
*Attorney, Agent, or Firm*—Finnegan, Henderson, Farabow, Garrett & Dunner

[57] ABSTRACT

A process for preparing hydroxylated aromatic compounds optionally bearing at least one trifluoromethyl, trifluoromethoxy or trifluoromethylthio group. A chloroformate or fluoroformate, optionally bearing at least one trihalomethyl-, trihalomethoxy- or trihalomethylthiophenyl group, is reacted with liquid hydrofluoric acid.

The aromatic compounds obtained are useful as synthesis intermediates in the pharmaceutical or the plant-protection industry.

10 Claims, No Drawings

PROCESS FOR PREPARING HYDROXYLATED AROMATIC COMPOUNDS

The present invention relates to a process for preparing hydroxylated aromatic compounds. More particularly, it relates to a process for preparing hydroxylated aromatic compounds bearing a trifluoromethyl unit.

It is known to prepare hydroxylated aromatic compounds, especially those containing trifluoromethyl groups, from trifluoromethylaniline, on which a diazotization reaction is carried out (Kirk Othmer, 10, p. 923).

It is also known from European Patent No. 19,388 to prepare hydroxylated aromatic compounds from a polyhalobenzene which, in a first stage, is brought together with an alkali metal hydroxide or alkaline earth metal hydroxide in a mixture of a polar aprotic solvent possessing a dielectric constant of between 30 and 70 and a hydroxylated solvent, the phenate originating from the first stage being brought into contact, in a second stage, with an acid to form the phenol.

The first method enables meta-trifluoromethylphenols to be synthesized.

The second process has the disadvantage of being of low selectivity, and hence of giving a large amount of isomers which are difficult to separate.

It is, in fact, always more advantageous to have available a method capable of selectively giving ortho-, meta- or para-trifluoromethylphenols.

The present invention has enabled an altogether new process to be found for the synthesis of a hydroxylated aromatic compound of the formula (I)

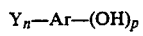

$$Y_n—Ar—(OH)_p \quad (I)$$

in which Y is selected from the group consisting of trifluoromethyl, trifluoromethoxy and trifluoromethylthio radicals, Ar is a mono- or polycyclic aromatic radical which may contain at least one substituent in addition to Y and (OH) and wherein the additional substituent may link the Y moiety to the Ar moiety, n is an integer equal to 0, 1 or 2, and p is an integer equal to 1 or 2, wherein a fluoroformate or chloroformate of the formula (II)

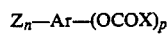

$$Z_n—Ar—(OCOX)_p \quad (II)$$

in which p and n have the same meaning as above, Z is selected from the group consisting of trihalomethyl, trihalomethoxy and trihalomethylthio radicals, Ar is a mono- or polycyclic aromatic radical which may contain at least one substituent in addition to Z and (OCOX), and wherein said additional substituent may link said Ar moiety to said Z moiety and X denotes chlorine or fluorine, is reacted with liquid hydrofluoric acid.

As expressed above, the Ar moiety in either formula (I) or (II) may contain at least one additional substituent other than those described above as Y, Z, (OH) or (OCOX). These additional substituents include all radicals which do not react in the present medium and are generally known to those skilled in the art, such as alkyl, alkoxy, halogen, alkylthio, phenyl, thiophenyl, phenoxy and nitro radicals. The additional substituents on Ar may also form a link between the Ar and Z moieties of formula (II), e.g., 4-(3-trichloromethylphenyl)-phenyl chloroformate is an illustrative compound of the formula (II), or between the Ar and Y moieties of formula (I).

Among the compounds of the formula (II), it is preferable to use those for which Ar is a phenyl group which may contain at least one substituent in addition to the Z and (OCOX) groups.

Among the phenyl fluoroformates or chloroformates of formula (II), it is preferable to use those for which n equals 1 and p equals 1.

Thus, it is especially advantageous to use trihalomethylphenyl, trihalomethoxyphenyl and trihalomethylthiophenyl fluoroformates or chloroformates.

It is preferable to use trichloromethylphenyl chloroformate.

The method of preparing compounds of the formula (II) is well-known to one skilled in the art. Representative compounds of formula (II) include:
4-Chlorophenyl chloroformate,
3-Trichloromethylphenyl chloroformate,
4-Trichloromethylphenyl chloroformate,
3-Trichloromethoxyphenyl chloroformate,
4-Trichloromethoxyphenyl chloroformate,
4-Trichloromethyl-2-chlorophenyl chloroformate,
4-Trichloromethyl-2,6-dichlorophenyl chloroformate,
4-Trichloromethoxy-2-chlorophenyl chloroformate,
3,4-Bis(trichloromethyl)phenyl chloroformate,
4-(3-Trichloromethylphenyl)phenyl chloroformate,
3-Trifluoromethylphenyl fluoroformate,
4-Trifluoromethyl-2-chlorophenyl fluoroformate,
3-Trifluoromethoxyphenyl fluoroformate,
4-Trifluoromethoxyphenyl fluoroformate,
4-Trichloromethylthiophenyl chloroformate,
3-Trichloromethylthiophenyl chloroformate,
4-Trifluoromethylthiophenyl fluoroformate,
3-Trifluoromethylthiophenyl fluoroformate,
p-Phenylene bis(chloroformate) and
m-Phenylene bis(fluoroformate).

Preferably, the molar ratio of hydrofluoric acid to the compound of formula (II) is from about 5 to 50, more preferably from 10 to 30.

It was discovered, quite surprisingly, that the addition of water accelerates the reaction of the phenyl fluoroformate or chloroformate with hydrofluoric acid. It is preferable to add an amount of water equal to at least about one mole per mole of compound of formula (II), but not exceeding 2 moles per mole of compound of formula (II).

It should be noted that a larger amount of water is not detrimental to the process of the invention, but contributes no additional advantage. In effect, the water and the hydrofluoric acid must then be separated.

The reaction may proceed under self-generated pressure.

The reaction temperature is preferably from about 20° to 150° C., more preferably, from 50° to 100° C.

When the temperature is higher than 20° C., the reaction preferably proceeds under pressure to maintain the hydrofluoric acid in liquid form.

The compounds of formula (I) originating from the present process are separated in a manner known per se, for example by distilling off the hydrofluoric acid present in the medium or by extraction using organic solvents.

The compounds originating from the present invention are used as synthesis intermediates in the pharmaceutical or the plant-protection industry (EP No. 54,149 and EP No. 49,383).

The examples which follow are given by way of example, and should not be regarded as limiting the invention.

EXAMPLE 1

M-TRIFLUOROMETHYLPHENOL 100 g (5 mol) of anhydrous hydrofluoric acid, 54.8 g (0.2 mol) of m-trichloromethylphenyl chloroformate and 7.2 g (0.4 mol) of water are introduced successively into a 250-ml stainless steel reactor stirred by means of a bar magnet. The reactor is closed and then brought gradually to a temperature of 80° C. for a total time of 3 hours 50 min. After being cooled to approximately 0° C. and decompressed, the crude acidic reaction product is poured into 200 g of crushed ice. The heterogeneous mixture thereby obtained is extracted with 3 times 100 cm³ of $CH_2Cl_2$, and the organic phases are combined, washed twice with 100 cm³ of water and then dried. After evaporation, 20 g of a compound consisting mainly of m-trifluoromethylphenol are recovered (analysis by infrared, gas chromatography and mass spectrometry).

EXAMPLE 2 m-TRIFLUOROMETHYLPHENOL

The procedure is identical to that in Example 1, with the following conditions and products:
Anhydrous hydrofluoric acid: 100 g (5 mol)
m-Trichloromethylphenyl chloroformate: 82.2 g (0.3 mol)
Water: 8.1 g (0.45 mol)
Temperature: 80° C.
Time: 4 hr 50 min After treatments and analyses (infrared, gas chromatography and mass spectrometry), 39 g of crude m-trifluoromethylphenol are recovered.

EXAMPLE 3 m-TRIFLUOROMETHYLPHENOL

The procedure is identical to that in Example 1, with the following conditions and products:
Anhydrous hydrofluoric acid: 50 g (2.5 mol)
m-Trichloromethylphenyl chloroformate: 41.1 g (0.15 mol)
Water: 3.6 g (0.2 mol)
Temperature: 60° C.
Time: 2 hours After treatments and analyses (infrared, gas chromatography and mass spectrometry), 19 g of crude m-trifluoromethylphenol are recovered.

EXAMPLE 4 p-TRIFLUOROMETHYLPHENOL

The procedure is identical to that in Example 1, with the following conditions and products:
Anhydrous hydrofluoric acid: 100 g (5 mol)
p-Trichloromethylphenyl chloroformate: 54.8 g (0.2 mol)
Water: 5.4 g (0.3 mol)
Temperature: 60° C.
Time: 4 hr 30 min After treatments and analyses (infrared, gas chromatography and mass spectrometry), 20 g of crude p-trifluoromethylphenol are recovered.

EXAMPLE 5 p-CHLOROPHENOL

The procedure is identical to that in Example 1, with the following conditions and products:
Anhydrous hydrofluoric acid: 60 g (3 mol)
p-Chlorophenyl chloroformate: 38.2 g (0.2 mol)
Water: 4.5 g (0.25 mol)
Temperature: 80° C.
Time: 4 hours After treatments and analyses (infrared, gas chromatography and mass spectrometry), 21 g of crude p-chlorophenol are recovered.

EXAMPLE 6 p-TRIFLUOROMETHOXYPHENOL

The procedure is identical to that in Example 1, with the following conditions and products:
Anhydrous hydrofluoric acid: 60 g (3 mol)
p-Trichloromethoxyphenyl chloroformate: 43.5 g (0.15 mol)
Water: 3.6 g (0.2 mol)
Time: 3 hours After treatment and analyses (infrared gas, chromatography and mass spectrometry), 18 g of crude p-trifluoromethoxyphenol are recovered.

I claim:

1. A process for preparing a hydroxylated aromatic compound of the formula (I)

$$Y_n\text{—}Ar\text{—}(OH)_p \qquad (I)$$

in which Y is selected from the group consisting of trifluoromethyl, trifluoromethoxy and trifluoromethylthio radicals, Ar is a mono- or polycyclic aromatic radical which may contain at least one substituent in addition to Y and (OH) and wherein said additional substituent may link said Y moiety to said Ar moiety, n is an integer equal to 0, 1 or 2, and p is an integer equal to 1 or 2, comprising the step of reacting a fluoroformate or chloroformate of the formula (II)

$$Z_n\text{—}Ar\text{—}(OCOX)_p \qquad (II)$$

in which p and n have the same meaning as above, Z is selected from the group consisting of trihalomethyl, trihalomethoxy and trihalomethylthio radicals, Ar is a mono- or polycyclic aromatic radical which may contain at least one substituent other than Z and (OCOX) and wherein said other substituent may link said Ar moiety to said Z moiety, and X denotes chlorine or fluorine, with liquid hydrofluoric acid.

2. The process of claim 1, wherein n equals 1 and p equals 1.

3. The process of claim 1, wherein Ar denotes an unsubstitued phenyl group.

4. The process of claim 1, wherein, in the formula (II), Z is a trihalomethyl group.

5. The process of claim 4, wherein Z is a trichloromethyl group.

6. The process of claim 1, wherein the molar ratio of hydrofluoric acid to the compound of formula (II) is from about 5 to about 50.

7. The process of claim 6, wherein said molar ratio is from 10 to 20.

8. The process of claim 1, wherein water is added in an amount ranging from at least one mole of water per mole of the compound of formula (II) to at most 2 moles of water per mole of the compound of formula (II).

9. The process of claim 1, wherein said reaction is conducted at a temperature ranging from about 20° to 150° C.

10. The process of claim 9, wherein said temperaturre ranges from 50° to 100° C.